(12) United States Patent
Nam

(10) Patent No.: US 7,947,314 B2
(45) Date of Patent: May 24, 2011

(54) SKIN WHITENING COSMETIC COMPOSITION, PACK CONTAINING THE SAME, AND PREPARATION METHOD THEREOF

(76) Inventor: Jong Hyun Nam, Seoul (KR)

( * ) Notice: Subject to any disclaimer, the term of this patent is extended or adjusted under 35 U.S.C. 154(b) by 175 days.

(21) Appl. No.: 12/159,119

(22) PCT Filed: Apr. 11, 2006

(86) PCT No.: PCT/KR2006/001317
§ 371 (c)(1),
(2), (4) Date: Jun. 25, 2008

(87) PCT Pub. No.: WO2007/074956
PCT Pub. Date: Jul. 5, 2007

(65) Prior Publication Data
US 2008/0299061 A1    Dec. 4, 2008

(30) Foreign Application Priority Data
Dec. 27, 2005  (KR) .................. 10-2005-0131063

(51) Int. Cl.
*A61K 36/00* (2006.01)
*A61K 36/13* (2006.01)
*A61K 35/12* (2006.01)

(52) U.S. Cl. ............. 424/725.1; 424/770; 424/520

(58) Field of Classification Search ............... None
See application file for complete search history.

(56) References Cited

U.S. PATENT DOCUMENTS

| 5,362,499 A * | 11/1994 | Lee ................ 424/547 |
| 7,166,281 B2 * | 1/2007 | Kennedy ........... 424/94.65 |
| 2004/0018159 A1 | 1/2004 | Shinpou |
| 2006/0153787 A1 | 7/2006 | Shinpou |

FOREIGN PATENT DOCUMENTS

| CN | 1271575 A | | 11/2000 |
| KR | 1020030039389 A | | 5/2003 |
| KR | 1020040082551 A | | 9/2004 |
| KR | 20050066142 A | | 6/2005 |
| WO | WO 2004/009108 | * | 1/2004 |

* cited by examiner

*Primary Examiner* — Christopher R. Tate
*Assistant Examiner* — Deborah A. Davis
(74) *Attorney, Agent, or Firm* — IpHorgan Ltd.

(57) ABSTRACT

A skin whitening cosmetic composition having excellent whitening effects without causing any side effects, which includes a carbonized pine cone, as well as a pack containing the same. The skin whitening cosmetic composition includes natural substances, unlike prior commercially available products, and has excellent whitening effects without causing any side effect since it is safe to the skin. When the whitening cosmetic composition is used as it is or as a pack together with a substrate, such as a nonwoven fabric, it will provide a functional pack that can impart whitening effects in addition to effects, such as skin moisturization and skin firming.

15 Claims, No Drawings

SKIN WHITENING COSMETIC COMPOSITION, PACK CONTAINING THE SAME, AND PREPARATION METHOD THEREOF

TECHNICAL FIELD

The present invention relates to a skin whitening cosmetic composition, a pack containing the same, and a preparation method thereof, and more particularly to a skin whitening cosmetic composition having excellent skin whitening effects without causing any side effects, which includes a carbonized pine cone, as well as a pack containing the same and a preparation method thereof.

BACKGROUND ART

The skin is a very important tissue that protects the human body in direct contact with the external environment and has biochemical and physical functions. Skin tissue is broadly divided into three parts: epidermis, dermis and hypodermis. Human skin color varies mainly depending on the number, size, type and distribution of melanosomes containing melanin within skin cells. The melanosomes are produced by melanin cells, and melanin is a black pigment produced in epidermis and is produced in melanocyte cells.

Melanin functions to protect deeper cells from UV light damage by absorbing UV light energy from sunlight. However, if the melanin is abnormally reduced, skin lesions, such as vitiligo, will occur, and on the contrary, if excessive melanin synthesis by UV and the like will damage the skin and form discolorations and freckles that can also cause skin cancer.

Human skin color is determined by various factors, among which the activity of melanocytes making melanin pigments, the distribution of blood vessels, the thickness of the skin, and whether the human body contains pigments, such as carotenoid and bilirubin, are important factors. Particularly, the most important factor is black pigment melanin that is produced by action of various enzymes, such as tyrosinase, in human melanocytes. The formation of this melanin pigment is influenced by physiological factors associated with, for example, genetic factors, hormone secretion and stress, and environmental factors such as UV light irradiation.

However, the excessive production and deposition of the melanin pigment cause skin abnormalities, such as skin darkening, discoloration, freckles and pigmentation. For this reason, in order to treat or reduce excessive melanin pigmentation caused by UV light exposure, ascorbic acid, kojic acid, arbutin, hydroquinone, glutathione or derivatives thereof, or substances having tyrosinase inhibitory activity, have been used in cosmetics or medical drugs, but have limited usability due to insufficient whitening effects, the problem of safety to the skin, and the problems of formulation and safety in cosmetics.

Recently, studies to find whitening active ingredients from natural substances have been continued. Among these ingredients, pluralities of plants extracts, including *Souhakuhi* extracts (Korean Patent Laid-Open Publication Nos. 99-002109 and 97-021273) were found to act on tyrosinase so as to inhibit the production of melanin. However, these extracts also have many problems in use at effective concentrations or higher in terms of stability, safety and discoloration possibility, and do not exhibit satisfactory effects.

Particularly when these whitening compositions are used in combination with a pack, they will be kept in direct contact with the skin for a given period of time because of the characteristics of the pack. Thus, they have disadvantages in that they will damage the soft skin or have an insufficient effect on restoration to a healthy and glossy skin, and in a severe case, artificial synthetic pack compositions can cause side effects, such as skin rashes or allergy. For this reason, attempts to use natural substances having moisturizing effects and excellent whitening effects in pack products have recently been increased.

Korean Patent Laid-Open Publication No. 2003-0039389 discloses a cosmetic composition for packs, including herbal and natural extracts. But, these natural substances do not have satisfactory skin whitening effects, and therefore, the development of a natural substance having satisfactory skin whitening effects is required.

Accordingly, the present invention have conducted to develop a whitening composition for packs, which has high skin whitening effects without causing any side effect on the human body, particularly the skin, due to the use of a natural substance, so that, when it is used as a general functional cosmetic composition or particularly used in packs, it will show surprising skin whitening effects, and at the same time, be safe for the skin. As a result, we have completed the present invention.

SUMMARY OF THE INVENTION

Therefore, it is an object of the present invention to provide a skin whitening cosmetic composition that has excellent skin whitening effects while being safe to the skin.

Another object of the present invention is to provide a functional pack that has excellent skin whitening effects and skin moisturizing effects while giving elasticity for the skin.

To achieve the above objects, the present invention provides a skin whitening cosmetic composition including a mixture of a carbonized pine cone, vegetable oil and a shellfish shell as effective components.

In the inventive composition, the mixture comprises a carbonized pine cone, vegetable oil and a shellfish shell in a weight ratio of 2~8:1~3:1~3. If the content of the carbonized pine cone is less than 2 weight ratios to the whole weight of the mixture, it will provide an insufficient effect, and if it is more than 8 weight ratios thereto, it will not show any increased effect.

The carbonized pine cones can be obtained by washing selected pine cones with water, drying the washed material, completely burning the dried material by heating in a closed container at a temperature of 100-300° C. for 3-10 hours, and sieving the burned material through a 50-200 mesh sieve so as to provide carbonized pine cone powder. The pine cone used as the material of the carbonized pine cone can be collected from a pine tree, the kind of which is not limited in the present invention.

The vegetable oil may be at least one selected from the group consisting of sesame oil, olive oil, perilla oil, coconut oil, castor oil, apricot seed oil, bean oil and seed oil.

The shellfish refers to animals having a shell, for example, calms or sea snails. In the present invention, bivalvia and gastropoda may all be used.

The shellfish shell can be obtained by boiling shellfish in soybean paste soup containing 10-20 wt % Korean soybean paste, at a temperature of 60-100° C. for about 1-3, removing the inner meat of the shellfish, completely drying the shell that remains, grinding the dried shell to a size of about 100-200 meshes, and then removing foreign substances from the powder.

Also, the whitening cosmetic composition according to the present invention may further includes additives, including a moisturizing agent, an emollient, a local irritant, a blood flow stimulant and a fragrance.

The additives can be used in an amount of 1-30 wt %.

Also, the inventive composition may additionally include hyaluronic acid, vitamin E or aroma essence oil.

The whitening cosmetic composition according to the present invention may be used as it is or as a pack obtained by allowing it to be absorbed into a substrate. Examples of the substrate, which can be used in the present invention, include cotton, a nonwoven fabric, a spunlace fabric, and pulp.

In another aspect, the present invention provides a method for preparing a whitening cosmetic composition, including the steps of: preparing a carbonized pine cone; obtaining vegetable oil; obtaining a shellfish shell; and adding an additive to a mixture of the carbonized pine cone, the vegetable oil and the shellfish shell.

In another aspect, the present invention provides a method for preparing a whitening pack, including the steps of: preparing a carbonized pine cone; obtaining vegetable oil; obtaining shellfish shell; adding an additive to a mixture of the carbonized pine cone, the vegetable oil and the shellfish shell; and allowing the mixture to be absorbed into a substrate.

In the mixture in the inventive method, the carbonized pine cone, the vegetable oil and the shellfish shell can be contained in a weight ratio of 2~8:1~3:1~3.

The description of the vegetable oil and the shellfish shell is as described above.

MODE FOR THE INVENTION

Hereinafter, the invention will be described in further detail.

As described above, the carbonized pine cone that is used as a main component in the inventive composition is in the form of carbonized pine cone powder that can be obtained by washing selected pine cones with water, drying the washed material, completely burning the dried material by heating in a closed container at a temperature of 100-300° C. for 3-10 hours, and sieving the burned material through a 50-200 mesh sieve.

The pine cone is a pine seed growing at a pine tree and will now be described in further detail. The pine tree is also called Sol, Chamsol, Songmok, Solnamoo, Sohorinamu in Korea. The pine tree is also called a red pine tree since its bark and a bud at the end of its shoot are red in color. In China, it is also called female pine, Yodong red pine, and short-leaf red pine. The pine tree is bifoliate, where two leaves form a couple. It is also called Isoosong, Ichimsong (denoting two-needle pine), Iripsong, etc. The scientific term of the pine tree is *Pinus densiflora* Siebold et Zuccarini. When the pine seed sprouts, cotyledons covered with the testa will come out above earth, and the number of the cotyledons is about 4 to 9 and is 6 in most cases. Pine leaves deviating the cotyledons form a couple and come out with one confronting the other and the bottom portion is in the vagina that is about 2 or 3 mm in size. The vagina is dark brown and is alive as long as the leaves, without falling down. Meanwhile, there are female and male flowers in pine, which bloom in the last ten days of April and the first ten days of May. The male flower is elliptical and 4 to 9 mm in length. The end of the stamen spreads in the shape of the half moon and there are two anthers below filaments. There are two wings in pollen. Meanwhile, 2 or 3 female flowers hang at the end of the branch. The initial shape is circular or elliptical and is about 5 mm in length and is light violet in color. This is a collection of a multitude of female flowers, which is called a cone. This is what is called a pine cone in the present invention. Mature pine cones consist of various scaly leaves, and in a scaly leaf, two ovules are in contact with each other, which later on become a seed with two wings. Young cones in spring before pollination are called storbile or conelet in English, instead of cones. Scaly leaves of the pine cone is in contact with the axis of the pine cone helically, its end is fat and big, its exposed part is near the diamond shape, and there is a protrusion in its center. When the pine cone is mature, the gap between scaly leaves becomes bigger and the seeds are fallen apart and come flying out.

The pine cone that is a raw material for preparing the carbonized pine cone can be collected from pine trees, the kind of which is not limited in the present invention. Examples of pine trees from which the pine cone can be collected include form a aurescens, form a anguina, var globosa, form a pendula, form a aggregata, form a biaggergata, form a erecta, etc.

The vegetable oil may be at least one selected from the group consisting of sesame oil, olive oil, perilla oil, coconut oil, castor oil, apricot seed oil, bean oil and seed oil. The vegetable oil used is prepared according to any conventional method known in the art or is commercially available.

For example, the sesame oil can be obtained by roasting sesame at a given temperature or higher and pressing the roasted sesame.

Sesame from which the sesame oil is obtained is an annual plant growing to a height of 90-150 cm and has short fuzz and long oval-shaped or willow leaf-like leaves that adhere while looking at each other. It has a soft eggplant-like color or a white color in summer while it contains seeds having colors varying depending on its varieties. The seeds are collected by cutting the stems in August or September when the fruits are ripened, drying the cut stems in a bundle in the sunlight, shaking the dried stems to collect the seeds and removing foreign matter. The black seed is used as a medicine, and the white seed is used as the raw material of oil. Oil squeezed from the dried seeds is used and this oil is slightly yellow in color and smells fragrant. It is miscible with ether, chloroform and petroleum ether and slightly dissolved in alcohol. Also, it hardens upon cooling at 0-5° C. Also, it has a specific gravity of about 0.9, a refractive index of about 1.5, an acid number of 2 or less, a saponification number of 188-195, and an iodine number of 103-116. Also, it contains glycerides such as oleic acid, linoleic acid, palmitic acid, stearic acid, arachidonic acid, lignoserinic acid. The non-saponified portions of the oil is present in an amount of 0.1-1.3% and include pytosterine, d-sesamine, sesamol, sesamoline, and vitamin E. Sesamol shows a red color by furfurol and concentrated hydrochloric acid, and this reaction is used to identify sesame oil. The effects of sesame are widely known also in the prior medical books. Particularly, black sesame has plain properties and is sweet and innoxious (Dongeuibogam). Also, it increases vigor, grows fat, replenishes marrow and brain tissue, strengthens muscles and bones, and softens the five viscera (Bongchogangmok). Also, it builds up marrow, replenishes sperm, extends life span, and makes a face color youthful looking. The black sesame oil acts to increase blood platelet so as to rapidly coagulate blood. Accordingly, it is sometimes used against idiopathic thrombocytopenia, haemorrhagic thrombocytopenia, and hemorrhagic diseases.

The olive oil refers to oil extracted from the fruit of an olive tree, which has an oil content of 30-70%. It is vegetable oil that has been used so long ago that it is recorded in the Old Covenant. It has a lemon yellow color, is odorless and has a simple taste. It can be classified into four categories: extra virgin, fine virgin, virgin and pure, in the order from the highest to the lowest purity. Also, it is divided into various grades according to temperature. Since an increase in the acidity of olive oil leads to a reduction in the fragrance and purity thereof, it measures the quality of olive oil. Olive oil is good for dieting and also has various effects, such as increasing endurance, reducing risk factors that can cause heart failure, and strengthening the immune system. Olive oil for use in the present invention can be extracted from the fruit of an olive oil by pressing or is commercially available.

The shellfish shell that is another element of the present invention can be obtained by boiling shellfish in soybean paste soup containing 10-20 wt % Korean soybean paste, at a temperature of 60-100° C. for about 1-3, removing the inner meat of the shellfish, completely drying the shell that remained, grinding the dried shell for the first time to a size of about 100-200 meshes, and then removing foreign substances from the powder. Then, in order to obtain fine powder through a secondary grinder (fine grinder), the above powder can be passed through a cyclone filter and a powder collection system to obtain high-purity fine powder having a size of about 200 meshes.

The shellfish refers to an animal having a shell, for example, a calm, sea snail or the like, and belonging to the phylum Mollusca. It is broadly divided into bivalvia and gastropoda. The bivalvia refers to shellfish having two shells, such as mussel, oyster, clam or the like, and the gastropoda refers to a class of shellfish having a snail-like shell, for example, sea snail, conch, mud snail or the like. Oyster is a food rich in phosphorus, potassium and vitamin A. In Chinese medicine, oyster is known to be used against fever and thirst and to provide a good complexion and aid nutrition. Mussels live stuck to sandy earth, rock and pile, scallops live on sandy bottom or gravelly field at a depth of 40 m from the water surface along the seashore, and calms are the most frequent typical bivalvia and live on sandy mud in a beach where fresh-water of 1-2 m is mixed.

Particularly, the shell of a sea squirt, a kind of gastropoda, contains large amounts of natural substances having excellent physiological functionality, for example, carotenoid pigments, inorganic components and taurine. The sea squirt shell is difficult to decompose because it is made of stone cells, but it contains large amounts of carotenoids, proteins and inorganic components, including calcium (Ca), phosphorus (P) and magnesium (Mg). Particularly, a natural carotenoid pigment can more preferably be used in the present invention, because it has been known as a carcinogenesis inhibitory substance through an epidemiological survey for 30 years and a recent verification experiment and known to show high-dimensional functionalities, such as antioxidant activity, improvement of the breeding and growth rate of animals, inhibition of disease occurrence, and improvement of meat color. Also, chondroitin sulfate extracted from the sea squirt shell is in the form of viscous liquid and known to have excellent effects for skin beauty, antiaging, arteriosclerosis inhibition, bone formation, inhibition of bacterial infection, etc.

Hereinafter, the present invention will be described in further detail with reference to Examples and Test Examples. It is to be understood, however, that these examples are for illustrative purposes only and are not to be construed limit the scope of the present invention.

EXAMPLE 1

Among the pine cones of a native kind of pine trees, pine cones having the desired size were selected. The selected pine cones were washed with purified water and dried in the shade. As the pine cones were completely dried, 1000 g of the dried pine cones were placed in a completely closed container, and then completely burned by heating at about 300° C. for about 8 hours. Thereafter, the burned pine cones were left to stand for 2 hours to cool the burned pine cones, thus obtaining carbonized pine cones. The carbonized pine cones thus obtained were sieved through a 100-mesh sieve, thus obtaining about 800 g of carbonized pine cone powder.

Sesame was screened through a screening machine so as to eliminate foreign matter, and the screened sesame was washed and sufficiently dried. After completion of the drying, it was roasted in a roaster at a temperature of about 160° C. until water was completely evaporated and just before smoke would be generated. The roasted sesame was crushed with a crusher, and sesame oil was extracted by pressing the sesame powder with a compressor.

100 g of a sea squirt was added to 1000 g of soybean paste soup containing 20 wt % soybean paste (Pulmuone Co.) and boiled at a temperature of 85° C. for about 2 hours. The shell that remained after removal of the inner meat of the sea squirt was completely dried for 2 hours and then ground for the first time to a size of 100 meshes, and then foreign matter was removed from the powder. Then, the powder was ground for the second time to a size of 200 meshes, thus obtaining 60 g of the sea squirt shell in the form of fine powder.

The carbonized pine cone, the sesame oil and the sea squirt shell powder were mixed with each other at a weight ratio of 6:2:2, and then conventional additives in an amount of 30 wt % were added to the mixture of carbonized pine cone, the sesame oil and the sea squirt shell powder. In this way, a skin whitening cosmetic composition was prepared.

EXAMPLE 2

The cosmetic composition prepared according to the method of Example 1 was applied to a nonwoven fabric, thus making a disposable pack.

EXAMPLES 3 TO 6

Whitening cosmetic compositions were prepared in the same manner as described in Example 1, except that composition ratios shown in Table 1 below were used.

TABLE 1

| Components | Example 3 (wt %) | Example 4 (wt %) | Example 5 (wt %) | Example 6 (wt %) |
|---|---|---|---|---|
| Carbonized pine cone | 60 | 50 | 60 | 70 |
| Sesame oil | | 20 | 30 | 20 |
| Olive oil | 20 | | | |
| Sea squirt shell powder | 20 | | 10 | 10 |
| Calm shell powder | | 30 | | |

TEST EXAMPLE 1

Whitening Effect

On 20 healthy men and women as subjects, a 1.5-cm-diameter opaque tape having five perforated holes was attached to both lower arms of each subject. Then, ultraviolet B light of about two times the minimum erythema dose was irradiated to each of the subjects to induce skin darkening.

Each of the compositions of Examples 1 and 2, Comparative Examples 1 (a mud pack manufactured by company A) and Comparative Example 2 (a mud pack manufactured by company B) was applied to the subjects two times each day for 4 weeks. After 4 weeks, the contrast of the skin was measured with a colorimeter.

Specifically, the colorimeter (e.g., Minolta $CR_2OO_2$) was used to measure the contrast of the skin, thus evaluating the effects of the compositions. The L*a*b* color system is generally used to measure color, and an L* value (brightness) was used as an index in this test example. The difference (L*) in skin color between a time point when the application of the test packs (Examples 1 and 2 and Comparative Examples 1 and 2) had been started and a time point when the application of the packs had been completed after 8 weeks was calculated and used to determine the effects of the packs. As a result, the whitening effect of the pack according to the present invention was shown as follows:

ΔL*=L* after application-L* value upon application

TABLE 2

| Test materials | ΔL* |
|---|---|
| Example 1 | 1.8 |
| Example 2 | 1.9 |
| Comparative Example 1 (manufactured by company A) | 0.95 |
| Comparative Example 1 (manufactured by company B) | 0.94 |

As can be seen in Table 2, the use of the pack according to the present invention resulted in a reduction in pigmentation.

TEST EXAMPLE 2

Skin Safety

In order to examine the skin irritation of the whitening cosmetic composition according to the present invention, a skin patch test using the whitening cosmetic compositions of Examples 1 to 3 and Comparative Examples 1 and 2 was performed on 15 women who were 30 years old. A patch containing 0.2 ml of each of the compositions was applied to the upper arm of each of the subject two times, and a skin reaction was examined within 1 hour after removal of the patch and examined again on the following day (after 48 hours). Skin irritability was evaluated based on the following standards. The evaluation results are shown in Table 3 below.
○: no change.
Δ: slight erythema is shown on the applied skin site.
X: clear erythema is shown on the applied skin site.

TABLE 3

| Examples | Irritability |
|---|---|
| Example 1 | ○ |
| Example 2 | ○ |
| Example 3 | ○ |
| Comparative Example 1 | ○ |
| Comparative Example 2 | Δ |

On 15 women in their middle thirties, the cosmetic compositions prepared according to Examples 1 and 2 were used continuously for 4 weeks together with the packs of Comparative Examples 1 and 2. The test subjects were unspecified women in their middle thirties and subjected to a blind test. The test results are shown in Table 4 below.

TABLE 4

| | Example 1 | Example 2 | Comparative Example 1 | Comparative Example 2 |
|---|---|---|---|---|
| Stability | ◎ | ◎ | Δ | X |
| Feeling | ◎ | ◎ | ○ | Δ |
| Whitening property | ◎ | ◎ | X | ○ |

(◎: very excellent; ○: excellent; Δ: common; and X: bad)

As is apparent from the above test results, the whitening cosmetic composition according to the present invention includes natural substances, unlike prior commercially available products, and has excellent whitening effects without causing any side effect since it is safe to the skin. When the inventive whitening cosmetic composition is used as it is or as a pack with a substrate, such as a nonwoven fabric, it will provide a functional pack that can impart a whitening effect in addition to effects, such as skin moisturization and skin firming.

Although a preferred embodiment of the present invention has been described for illustrative purposes, those skilled in the art will appreciate that various modifications, additions and substitutions are possible, without departing from the scope and spirit of the invention as disclosed in the accompanying claims.

The invention claimed is:

1. A skin whitening cosmetic composition comprising a mixture of a carbonized pine cone, vegetable oil and a sea squirt shell as effective components, wherein the mixture comprises the carbonized pine cone, vegetable oil and sea squirt shell in a weight ratio of 2~8:1~3:1~3.

2. The composition of claim 1, wherein the carbonized pine cone is a carbonized pine cone powder obtained by washing selected pine cones with water, drying the washed material, completely burning the dried material by heating in a closed container at a temperature of 100-300° C. for 3-10 hours, and sieving the burned material through a 50-200 mesh sieve.

3. The composition of claim 1, wherein vegetable oil may be at least one selected from the group consisting of sesame oil, olive oil, perilla oil, coconut oil, castor oil, apricot seed oil, bean oil and seed oil.

4. The composition of claim 1, wherein the sea squirt shell is in the form of powder obtained by boiling sea squirt in soybean paste soup containing soybean paste, removing the inner meat of the boiled sea squirt and grinding the shell that remained.

5. The composition of claim 1, wherein the sea squirt shell is in the form of powder obtained by boiling sea squirt in soybean paste soup containing 10-20 wt % soybean paste, at a temperature of 60-100° C. for about 1-3, removing the inner meat of the sea squirt, completely drying the shell that remained, grinding the dried shell for the first time to a size of about 100-200 meshes.

6. The composition of claim 1, which further comprises at least one additive selected from the group consisting of a moisturizing agent, an emollient, a local irritant, a blood flow stimulant and a fragrance.

7. The composition of claim 6, wherein the additive is contained in an amount of 1-30 wt %.

8. The composition of claim 1, which further comprises at least one selected from the group consisting of hyaluronic acid and vitamin E.

9. A pack comprising a whitening cosmetic composition according to any one of claims 1 to 8 and a substrate.

10. The pack of claim 9, wherein the substrate is cotton, a nonwoven fabric, a spunlace fabric, and pulp.

11. A method for preparing a whitening cosmetic composition, the method comprising the steps of:
preparing a carbonized pine cone;
obtaining vegetable oil;
obtaining a sea squirt shell; mixing the carbonized pine cone, vegetable oil and sea squirt shell and
adding additives to the mixture of the carbonized pine cone, the vegetable oil and the sea squirt shell.

12. The method of claim 11, wherein the mixture comprises the carbonized pine cone, the vegetable oil and the sea squirt shell in a weight ratio of 2~8:1~3:1~3.

13. A method for preparing a whitening cosmetic pack, the method comprising the steps of:
preparing a carbonized pine cone;
obtaining vegetable oil;
obtaining a sea squirt shell; mixing the carbonized pine cone, vegetable oil and sea squirt shell,
adding additives to the mixture of the carbonized pine cone, the vegetable oil and the sea squirt shell; and
allowing the mixture to be absorbed into a substrate.

14. The method of claim 13, wherein the mixture comprises the carbonized pine cone, the vegetable oil and the sea squirt shell in a weight ratio of 2~8:1~3:1~3.

15. The composition of claim 1, wherein vegetable oil comprises sesame oil.

* * * * *